(12) United States Patent
Mallozzi et al.

(10) Patent No.: US 10,509,465 B1
(45) Date of Patent: Dec. 17, 2019

(54) MOUTH OPERATED INPUT SYSTEM

(71) Applicants: Adriana Mallozzi, Brookline, MA (US); Shana Penna, Brookline, MA (US); Jiahao Zhao, Chelsea, MA (US); Elijah Tucker, Maynard, MA (US); Marian Heman-Ackah, Jamaica Plain, MA (US)

(72) Inventors: Adriana Mallozzi, Brookline, MA (US); Shana Penna, Brookline, MA (US); Jiahao Zhao, Chelsea, MA (US); Elijah Tucker, Maynard, MA (US); Marian Heman-Ackah, Jamaica Plain, MA (US)

( * ) Notice: Subject to any disclaimer, the term of this patent is extended or adjusted under 35 U.S.C. 154(b) by 0 days.

(21) Appl. No.: 16/177,223

(22) Filed: Oct. 31, 2018

(51) Int. Cl.
    *G06F 3/01* (2006.01)
(52) U.S. Cl.
    CPC ................... *G06F 3/011* (2013.01)
(58) Field of Classification Search
    None
    See application file for complete search history.

(56) References Cited

U.S. PATENT DOCUMENTS

| 5,460,186 A * | 10/1995 | Buchhold ............... A61F 4/00 340/4.11 |
| 6,222,524 B1 * | 4/2001 | Salem .................... A61F 4/00 340/4.11 |
| 2007/0206274 A1 * | 9/2007 | Nakamura ......... G02B 21/0012 359/379 |
| 2014/0354397 A1 * | 12/2014 | Quintal, Jr. ............ G05G 9/047 340/4.11 |

* cited by examiner

*Primary Examiner* — Nicholas J Lee
(74) *Attorney, Agent, or Firm* — Gulf Coast Intellectual Property Group (57) ABSTRACT

A mouth operated input system that includes a controller and a mouth operated input device that is operably coupled to at least one device so as to provide input control thereof. The mouth operated input device includes a joystick module and an activation module operably coupled thereto. The activation module includes an activation module control board and further has mounted thereto a first actuator and a second actuator. The first actuator is mounted to be engaged by a user's mouth. The second actuator is mounted to the housing of the activation module and is configured as an optical switch. The activation module is movable in all directions so as to provide movement of the joystick operably coupled thereto. The controller of the present invention includes a database that stores input data from the joystick module and the first and second actuators. Multiple modes of operation are provided by the controller.

20 Claims, 4 Drawing Sheets

MOUTH OPERATED INPUT SYSTEM

PRIORITY UNDER 35 U.S.C Section 119(e) & 37 C.F.R. Section 1.78

This nonprovisional application claims priority based upon the following prior U.S. Provisional Patent Application entitled: Mouth Operated Input Device, Application No.: 62/580,793 filed Nov. 2, 2017, in the name of Adriana Mallozzi, et. Al., which is hereby incorporated by reference for all purposes.

FIELD OF THE INVENTION

The present invention relates generally to input devices, more specifically but not by way of limitation, a mouth operated input system that includes a mouth operated input device and operating software interface wherein the system is configured to provide control of apparatus such as but not limited to assistive apparatus.

BACKGROUND

Various types of assistive apparatus for physically challenged individuals are known in the art. Individuals that have significant physical disabilities utilize assistive apparatus such as but not limited to motorized wheelchairs to provide independent mobility for the user thereof. These devices are conventionally controlled by various interfaces such as but not limited to arm mounted joysticks, buttons, oral interfaces and the like. For many users, these conventional controls do not provide the best technique to interface with and control the apparatus.

Some individuals require alternate interface techniques that are more suited to their specific needs. Examples of existing technology include voice recognition technology and mouth operated devices. Mouth operated devices facilitate interface with a device such as but not limited to an assistive apparatus and provide a user with limited limb mobility a technique to control various apparatus. While some mouth operated input devices are known in the art, deficiencies in the field include but are not limited to the ability to control more than one device simultaneously and provide a plurality of actuators to operably engage various apparatus.

Accordingly, there is a need for a mouth operated input system that includes a device having a plurality of actuators configured to provide control of a single device and/or provide the ability to interface with and control more than one device. Additionally, a software interface that provides learned user behavior and a adaptive reaction thereto.

SUMMARY OF THE INVENTION

It is the object of the present invention to provide a mouth operated input system that includes a mouth operated input device and a software wherein the mouth operated input system can be operably coupled to apparatus such as but not limited to assistive apparatus and personal electronics.

Another object of the present invention is to provide a mouth operated input system configured to provide interface control of at least one apparatus wherein the mouth operated input device includes a plurality of actuators wherein the plurality of actuators employ alternate technologies for activation thereof.

A further object of the present invention is to provide a mouth operated input system operable to assist a user in controlling apparatus such as but not limited to assistive apparatus wherein the mouth operated input device includes a mounting arm having a joystick module coupled to an end thereof.

Still another object of the present invention is to provide a mouth operated input system configured to provide interface control of at least one apparatus wherein the mouth operated input device includes an activation module operably coupled to the joystick module.

An additional object of the present invention is to provide a mouth operated input system operable to assist a user in controlling apparatus such as but not limited to assistive apparatus wherein the mouth operated input device includes wherein the activation module includes at least two actuators that are configured to provide operational control of an apparatus utilizing different techniques.

Yet a further object of the present invention is to provide a mouth operated input system configured to provide interface control of at least one apparatus wherein the mouth operated input device includes a communication control board disposed therein wherein the communication control board facilitates wireless communication with various apparatus.

Another object of the present invention is to provide a mouth operated input system operable to assist a user in controlling apparatus such as but not limited to assistive apparatus that further includes at least one biometric sensor.

Still an additional object of the present invention is to provide a mouth operated input system configured to provide interface control of at least one apparatus wherein the software of the present invention further provides the ability to measure at least one biometric parameter of a user and offer adaptive interface levels based thereon.

Yet another object of the present invention is to provide a mouth operated input system operable to assist a user in controlling apparatus such as but not limited to assistive apparatus wherein the activation module is movably engaged with the joystick module.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Referring now to the drawings submitted herewith, wherein various elements depicted therein are not necessarily drawn to scale and wherein through the views and figures like elements are referenced with identical reference numerals, there is illustrated a mouth operated input system 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Figure 1:
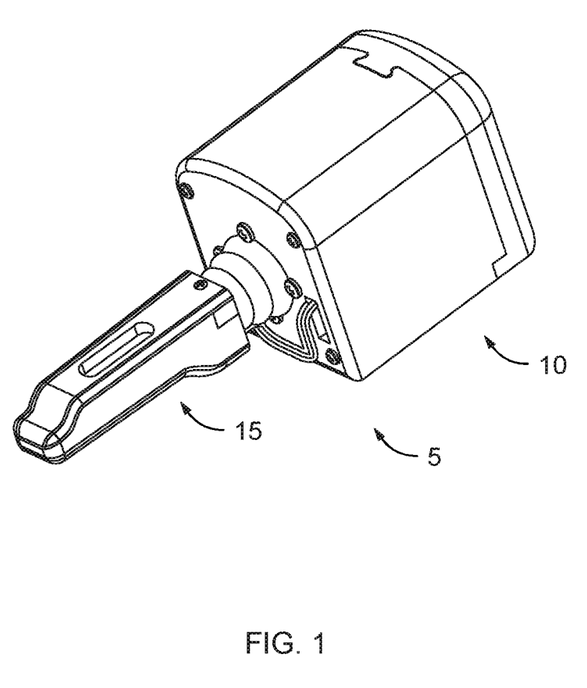
FIG. 1 is a perspective view of the mouth operated input device of the present invention.

Referring in particular to FIG. 1 the mouth operated input system 100 includes a mouth operated input device 5 wherein the mouth operated input device 5 includes a joystick module 10 and an activation module 15. As further discussed herein, the joystick module 10 is moveably coupled to the activation module 15. The joystick module 10 is operably coupled to an arm member 17 wherein the arm member 17 provides a technique of mounting the mouth operated input device 5 to a device such as but not limited to an assistive device. The arm member 17 is manufactured from a resilient durable material such as but not limited to metal. The arm member 17 is operable to position the mouth operated input device 5 in a desirable position so as to be engaged by a user. It is contemplated within the scope of the present invention that the arm member 17 could be constructed from various suitable materials and alternate lengths in order to accomplish the desired objective described herein.

Figure 2:
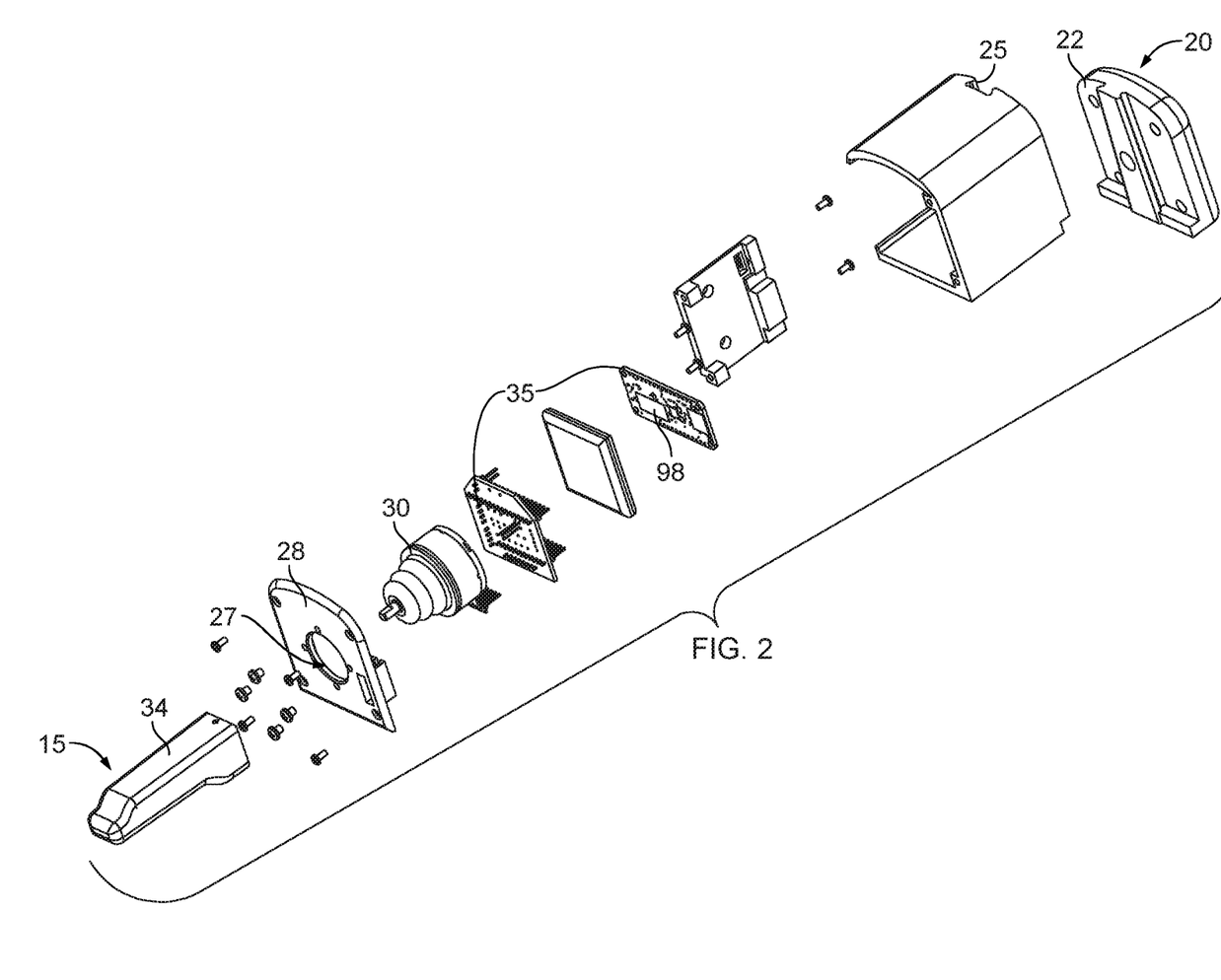
FIG. 2 is an exploded view of the mouth operated input device of the present invention.

The joystick module 10 includes a base member 20 that is releasably secured to the arm member 17 utilizing suitable techniques such as but not limited to threads 21. The base member 20 is coupled to a mounting member 25 wherein the mounting member 25 is secured to the first surface 22 of the base member 20 utilizing a dovetail shaped channel and mateable magnets embedded in the base member 20 and mounting member 25. The base member 20 is rounded in shape and is manufactured from a durable material such as but not limited to plastic. The mounting member 25 is manufactured from the same material and includes a cavity 26 with an aperture 27 centrally located therein. The cavity 26 includes wall 28 that is sloped outward in form defining the shape of the cavity 26 wherein the shape thereof permits full rotational movement of the joystick 30 that is journaled through the aperture 27. While the mounting member 25 is illustrated having a cavity 26 and wall 28 of a specific shape, it is further contemplated within the scope of the present invention that the mounting member 25 could be constructed having a flat upper surface. The joystick 30 is operably coupled to control module 35 wherein the control module 35 includes the necessary electronics to store, receive, transmit and manipulate data so as to translate movement of the joystick 30 into an actionable movement of a device such as but not limited to provide adaptive control of inputs for a computing device.

Figure 3:
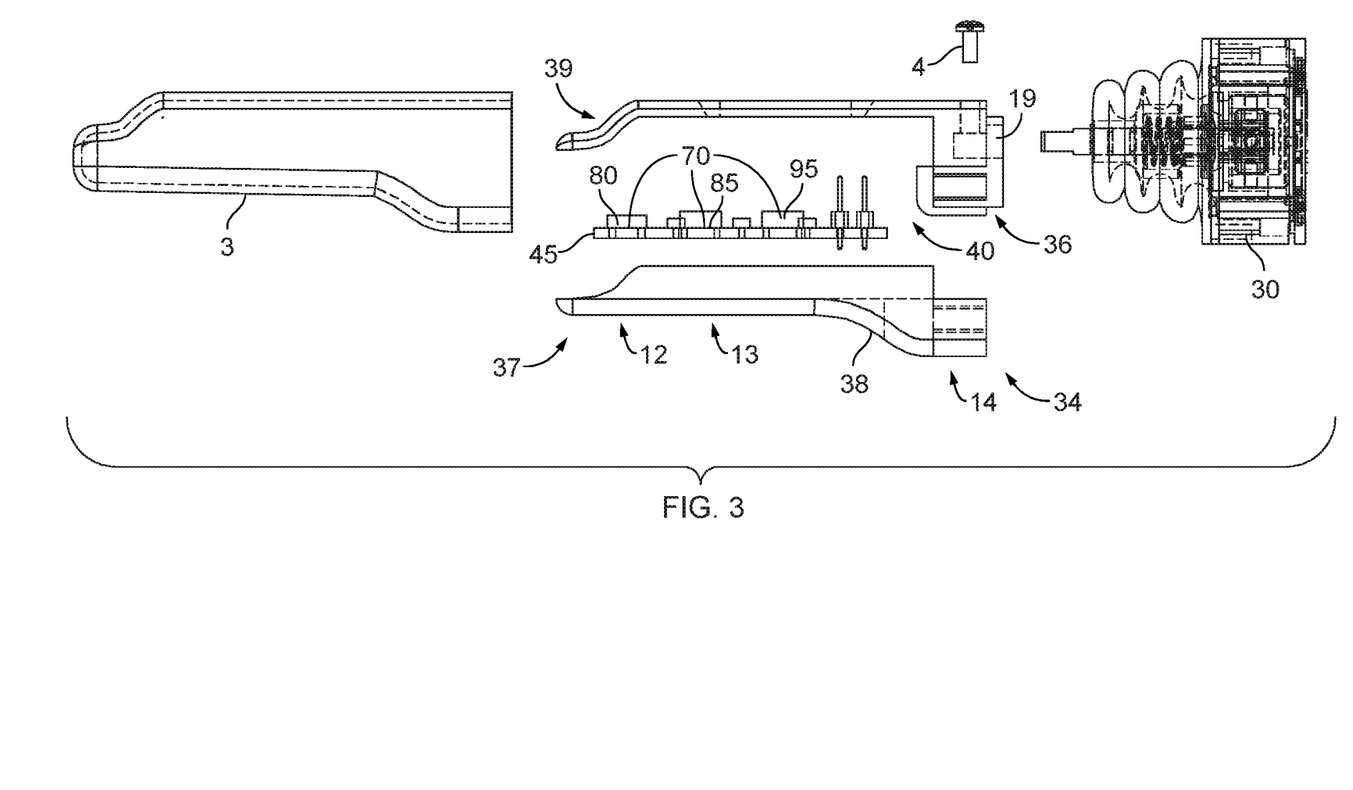
FIG. 3 is an exploded view of the activation module of the present invention.

The activation module 15 includes a housing 34 that is comprised of an upper portion 36 and a lower portion 37. The housing 34 is manufactured from a suitable durable material such as but not limited to plastic, and is covered by a flexible, optically-clear, and bacteria-resistant covering 3 constructed out of silicone or similar material. Housing portion 3 includes a sloped, forward edge 39 at the front of the upper portion 36, along with a sloped, rear edge 38 at the back end of the lower portion 37. Sloped rear edge 38 and the form thereof is further discussed herein pertaining to second actuator 85. The upper portion 36 and a lower portion 37 of the housing 34 form an interior volume 40 that is of suitable size so as to accommodate an activation module control board 45. Activation module control board 45 is a conventional computing control board having the necessary electronics to store, receive, transmit and manipulate data. The activation module control board 45 provides operational control of the activation module 15 and the actuators 70 integrally formed therewith.

The housing 34 of the mouth operated input device 15 includes a first portion 12, a second portion 13 and a third portion 14 wherein the immediately aforementioned are contiguously formed. The first portion 12 and second portion 13 is configured to be at least partially inserted into a user's mouth. The end of the housing 34 further includes receiving cavity 19. Receiving cavity 19 is formed so as to mate and securely receive therein at least a portion of joystick 30. The joystick 30 is secured to the receiving cavity 19 by a set screw 4. The activation module 15 is movably mounted upon the wall 28 wherein the movement thereof is translated through joystick 30. Movements of the joystick 30 are interpreted by input device control board 35 so as to execute a repeated motion in an assistive device.

The module 15 includes a first actuator 80 that is integrally mounted to the lower portion 37 of the housing 34. The first actuator 80 is a variable pressure tactile button that is configured to be pressed in order to provide activation of an operably coupled device as is further discussed herein. The pressure required to engage the first actuator 80 is variably controlled by either electronic or mechanical techniques. It is contemplated within the scope of the present invention that the first actuator 80 is engaged by a user's mouth wherein the first actuator 80 is depressed inward by a user's mouth so as to provide at least one operational control task of a device operably coupled to the mouth operated input device 5. It is contemplated within the scope of the present invention that the first actuator 80 could be operably coupled to a device such as but not limited to a computing device. The first actuator 80 is additionally configured to measure the pressure applied thereto upon depression thereof. The pressure which can be measured in pounds per square inch is recorded in the memory of the input device control board 35 and subsequently utilized for analysis of user condition facilitating adaptability. As will be further discussed herein, the mouth operated input system 100 captures data such as the aforementioned bite pressure on the first actuator 80 in order to determine a user's potential physical condition. The input device control board 35 is operably coupled to the first actuator 80 and can vary the required downward force by a user's mouth in order to provide activation of the first actuator 80. By way of example but not limitation, if the mouth operated input system 100 detects that a user is in a weakened condition and cannot exert as much pressure with their mouth on the first actuator 80, the input device control board 35 places the first actuator 80 in a second mode wherein the pressure required to activate the first actuator 80 is less than that required in a first mode of the first actuator 80. The input device control board 35 is configured to store and transmit bite pressure data from the first actuator 80 wherein the software of the present invention maintains a data log thereof and establishes ranges in order to execute transition of the first actuator 80 intermediate its first mode and second mode. The first actuator 80 is operably coupled with the input device control board 35 wherein the input device control board 35 relays the signal from the first actuator 80 to the wireless communication module 98 in order to transmit the signal to an operably coupled device.

The second actuator 85 is integrally mounted to the lower portion 37 of the housing 34. The second actuator 85 is an optical switch that is communicably coupled to the input device control board 35. The second actuator 85 includes an on command and an off command that is controlled by the amount of light being received thereby. In a preferred embodiment of utilization of the present invention, it is contemplated that the second actuator 85 is operably engaged by movement of a user's lips ensuing insertion of the first portion 12 and second portion 13 of the housing 34 into the mouth of a user. Subsequent insertion of the first portion 12 and the second portion 13, the third portion 14 is adjacent a user's lips. The sloped backwards edge 38 is shaped so as to facilitate improved engagement by a user's upper lip. In use, a user will anchor their lower lip and move their upper lip so as to engage the second actuator 85 to activate the on or off position thereof. Sliding a portion of the upper lip provides coverage of the second actuator 85 so as to alter the position, either off or on, thereof. The second actuator 85 is operably coupled to the activation module control board 45 and the communication module 98 in order to provide either control of a second operably coupled device or an additional command of an operably coupled device.

The activation module 15 further includes a biometric sensor 95. The biometric sensor 95 is operably coupled to the activation module control board 45 and is configured to detect model parameters such as but not limited to respiratory rate, heart rate, body temperature or bite pressure. It is contemplated within the scope of the present invention that the mouth operated input system 100 could employ more than one biometric sensor 95. As is further discussed herein, the biometric sensor 95 receives and transmits data to the activation module control board 45 for analysis and interpretation of the user's physical status and subsequently makes accommodations based thereon. It is contemplated within the scope of the present invention that the biometric sensor 95 could be place in alternate locations on the activation module 15 and provide more than one biometric measurement. As will be further discussed herein the software of the present invention collects and stores data from the biometric sensor 95 in order to transition the mouth operated input system 100 intermediate a first mode and a second mode wherein in the second mode the mouth operated input system 100 makes adjustments requiring less input in order to provide the necessary control signal to an operably coupled device. By way of example but not limitation, ensuing transition into the second mode the movement speed and/or amount of the activation module 15 by a user thereby moving joystick 30 is such that the speed and/or amount to obtain the desired action of the operably coupled device is less. If the mouth operated input system 100 is operably coupled to a motorized mobility device and the user is utilizing the joystick module 10 to provide operable control thereof, the second mode of the mouth operated input system 100 would require less input to achieve the same effect on the motorized mobility device.

Figure 4:
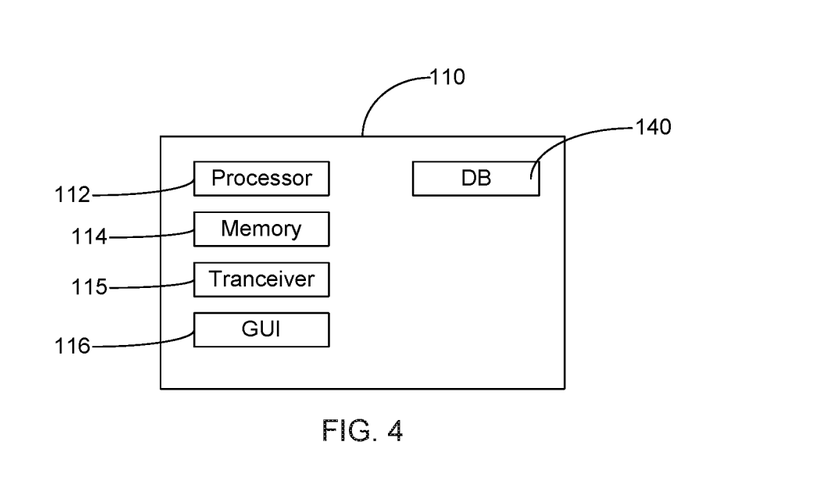
FIG. 4 is a block diagram of the controller of the present invention.

Referring to FIGS. 3 and 4 herein, a schematic block diagram of the software and controller 110 is illustrated therein. The mouth operated input system 100 includes a controller 110 that is a conventional computing device such as but not limited to a smart phone or tablet PC. The controller 110 includes conventional components such as a processor 112, memory 114, transceiver 115 and a graphical interface 116 wherein the aforementioned combine to provide operational control of the mouth operated input device 5. The controller 110 further includes a database 140 wherein the database 140 provides storage and analysis of the input parameters setting model from the actuators 70 and the joystick module 10 wherein the data is time oriented and control charts are established thereon. As is discussed herein the data is utilized to determine when to transition the mouth operated input device 5 intermediate its first mode and second mode based on user current user input. It is contemplated within the scope of the present invention that the controller 110 is operably coupled to the mouth operated input device 5 utilizing conventional wireless communication protocols.

The controller 110 executes the desired functionality of the mouth operated input device 5 such as but not limited to operable coupling with devices, calibration of the mouth operated input device 5, user settings, mode selection and/or confirmation and profile selection. As previously discussed herein the mouth operated input system 100 is operable in a first mode and a second mode. In the first mode the mouth operated input system 100 functions utilizing default settings. By way of example but not limitation, the first mode of operation of the mouth operated input system 100 would include no adjustment to the settings of the first actuator 80 or the joystick module 10 as it pertains to the operational movement required to engage therewith. The controller 110 collects data from the biometric sensor 95, first actuator 80 and joystick module 10 and maintains input values therefrom. Each input value is evaluated against an established data set wherein the established data sets model parameters from the aforementioned for at least twenty days of utilization.

Ensuing collection of the input values and average for each model parameter is established. The controller 110 subsequently compares the input for model parameters during daily use to the established statistically significant average. If at least one of the model parameters is less than the statistically significant percent of the established average the controller 110 will place the mouth operated input system 100 into its second mode. It should be understood that twenty five percent is utilized in an exemplary manner and does not serve to provide limitation and it is contemplated that alternate percentages could be utilized. In the second mode the input required for the mouth operated input device 5 is less than that of the input required in its first mode. By way of example but not limitation, if the bite pressure measured on the first actuator 80 is less than the statistically significant average set by the model parameters of the established bite pressure average, then the controller 110 will transmit a signal to the activation module control board 45 to alter the switch tension of the first actuator 80 so as to require less bite pressure in order to execute an input command from a user. A similar technique is executed with the joystick module 10. It should be understood that the data point will be set by the model parameters that reflect less than the established statistically significant average is utilized for exemplary purposes only and the mouth operated input system 100 could be transitioned from its first mode to its second mode utilizing alternate variance from the established input averages. It should be further understood within the scope of the present invention that the transition intermediate the first mode and second mode could occur if the engagement with the first actuator 80 is more than the statistically significant average set by the model parameters.

Figure 5:
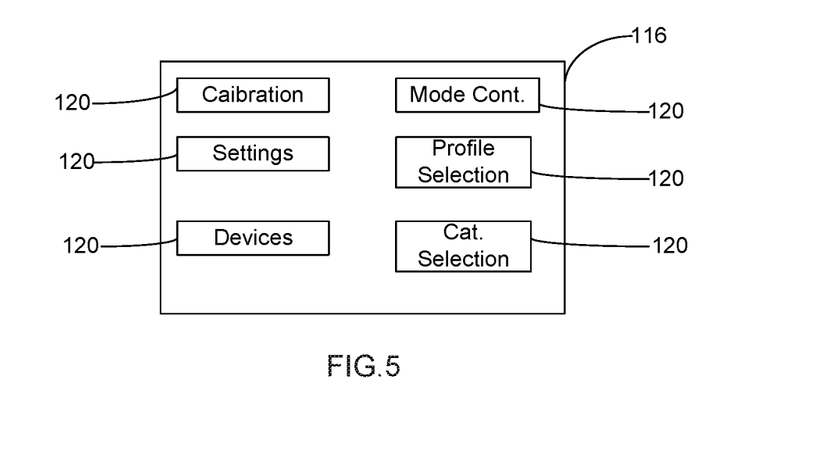
FIG. 5 is a block diagram of the graphical interface of the controller.

It is further contemplated within the scope of the present invention that the controller 110 could provide a prompt to a user so as to confirm transition intermediate the first mode and second mode of the mouth operated input system 100. Additionally, the controller 110 provides via an icon 120 an option for a user to select a category wherein the mouth operated input system 100 has predetermined categories such as but not limited to easy or difficult wherein the categories have a corresponding input parameter requirement for the mouth operated input device 5. The categories provide a technique for the user of the mouth operated input system 100 to initiate selection based on their current preference or daily physical condition.

The controller 110 further facilitates the operation of a third mode of the mouth operated input system 100. In its third mode the mouth operated input system 100 is operably coupled with at least two devices. By way of example but not limitation, in its third mode the mouth operated input system 100 could be operably coupled to a motorized mobility device and a cellular phone. In the third mode, the first actuator 80 or the second actuator 85 is operably coupled to an alternate device from the joystick module 10. An exemplary configuration of the third mode of the mouth operated input system 100 would include the first actuator 80 is operably coupled to a cellular phone wherein depressing the first actuator 80 would answer an incoming call on the cellular phone while the joystick module 10 and the second actuator 85 are operably coupled to the motorized mobility device so as to provide control thereof. It is contemplated within the scope of the present invention that in the third mode of the mouth operated input system 100 an operable connection could be established with numerous types of devices.

While the mouth operated input system 100 has been disclosed herein in its preferred embodiment wherein a user engages therewith utilizing their mouth, it is contemplated within the scope of the present invention that the mouth operated input system 100 could be engaged with a user's hand in addition to a user's mouth. By way of example but not limitation, the first actuator 80 and the second actuator 85 could be configured to be engaged by a user's finger wherein the activation module 15 is sized so as to engage with a user's hand. In a hand engagement configuration a user could utilize a finger to cover/uncover the second actuator 85 so as to engage the optical functionality thereof.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An input system operably coupled to at least one apparatus and configured to provide inputs thereto comprising:
  a controller, said controller having an operating software configured to provide operation of the mouth operated input system, said controller having the necessary electronics to receive, store, transmit and manipulate data;
  an input device, said input device operably coupled to said controller, said mouth operated input device having a joystick module and an activation module, said activation module operably coupled to said joystick module, said activation module having a portion that is configured to be engaged by a user, said activation module having an activation module control board disposed therein, said activation module having a plurality of actuators, said plurality of actuators being operably engaged through different techniques, said plurality of actuators operably coupled to said activation module control board, said plurality of actuators configured to generate a signal ensuing engagement thereof, said signal from said plurality of actuators transmitted to at least one apparatus so as to provide an input command providing control thereof; and
  wherein the input system includes a first mode of operation and a second mode of operation.

2. The input system as recited in claim 1, wherein one of said plurality of actuators is a tactile button that is positioned on the activation module so as to be engaged by a user's mouth or finger.

3. The input system as recited in claim 2, wherein said activation module includes a housing, said housing having an interior volume, said activation module control board being disposed therein, wherein one of said plurality of actuators is located on the lower portion of the housing.

4. The input system as recited in claim 3, wherein the actuator on the lower portion of the housing is an optical switch, wherein the optical switch is positioned to be engaged by a portion of a user's lips or finger.

5. The input system as recited in claim 4, and further including at least one biometric sensor, said at least one biometric sensor being operably coupled to said activation module control board, said at least one biometric sensor being disposed on said housing of said activation module.

6. The input system as recited in claim 5, and further including a database, said database operable to store input data from said joystick module and said plurality of actuators.

7. The input system as recited in claim 6, wherein in said second mode the input system provides control of the at least one apparatus with a lower value of input from a user to the plurality of actuators and the joystick module.

8. A mouth operated input system that is operably coupled to at least two devices so as to provide operational input thereto wherein the mouth operated input system includes a first mode and a second mode comprising:
   a mouth operated input device, said mouth operated input device having a joystick module and an activation module, said joystick module and said activation module being movably coupled, said activation module having a housing forming an interior volume, said housing of said activation module having a first portion, a second portion and a third portion being contiguously formed, said third portion of said housing of said activation module being operably coupled with a joystick of said joystick module, said activation module having a activation module control board disposed in said interior volume, said activation module control board having the necessary electronics to store, receive, transmit and manipulate data signals;
   a first actuator, said first actuator being operably coupled to the activation module control board and mounted to the first portion of the housing of the activation module, said first actuator configured to receive a tactile input from a user so as to provide input control to one of the at least two devices to which the mouth operated input system is operably coupled;
   a second actuator, said second actuator being operably coupled to the activation module control board, said second actuator being mounted to the housing of said activation module, said second actuator configured to receive input from a user so as to provide input control to one of the at least two devices to which the mouth operated input system is coupled; and
   a controller, said controller having an operating software configured to provide operation of the mouth operated input device, said controller having the necessary electronics to receive, store, transmit and manipulate data, said controller providing a graphical interface to the user for access to the operating software thereof, said controller further including a database.

9. The mouth operated input system as recited in claim 8, wherein the second actuator is an optical switch configured to receive input by coverage thereof from a portion of a user's lips.

10. The mouth operated input system as recited in claim 9, wherein in the first mode the mouth operated input device utilizes default settings for input control of the first actuator and the joystick module.

11. The mouth operated input system as recited in claim 10, wherein the database receives and stores time oriented input data from said joystick module and said first actuator.

12. The mouth operated input system as recited in claim 11, wherein in the second mode, the first actuator and the joystick module require an input value that is less than that of the input value required in the first mode.

13. The mouth operated input system as recited in claim 12, and further including a third mode, in said third mode said activation module is operably coupled to a first device and a second device wherein engagement with the first actuator provides operational input to the first device and engagement with the second actuator or the joystick module provides operational input to the second device.

14. The mouth operated input system as recited in claim 13, wherein the first actuator is a variable pressure tactile button.

15. A mouth operated input system that is operably coupled to at least two devices so as to provide operational input thereto wherein the mouth operated input system includes a first mode and a second mode comprising:
   a mouth operated input device, said mouth operated input device having a joystick module and an activation module, said joystick module and said activation module being movably coupled, said joystick module having a base member being secured to a flexible arm member, said joystick module further having a mounting member secured to said base member opposite said arm member, said mounting member having a central aperture, said mounting member having a cavity and an opening providing access thereto, said joystick module having a joystick extending into said cavity, said activation module having a housing forming an interior volume, said housing of said activation module having a first portion, a second portion and a third portion being contiguously formed, said second portion being intermediate said first portion and said third portion, said first portion having a front sloped wall, said third portion of said housing of said activation module being operably coupled with a joystick of said joystick module, said activation module having an activation module control board disposed in said interior volume, said control board having the necessary electronics to store, receive, transmit and manipulate data signals;
   a first actuator, said first actuator being operably coupled to the activation module control board and mounted to the lower portion of the housing of the activation module, said first actuator configured to receive a tactile input from a user so as to provide input control to a first device to which the mouth operated input system is operably coupled, said first actuator configured to require variable pressure from a user's mouth engaged therewith in order to provide activation thereof;
   a second actuator, said second actuator being operably coupled to the activation module control board, said second actuator being mounted to the lower portion of the second portion of the housing of said activation module, said second actuator configured to receive input from a user so as to provide input control one of the at least two devices to which the mouth operated input system is coupled, said second actuator being an optical switch; and
   a controller, said controller having an operating software configured to provide operation of the mouth operated input device, said controller having the necessary electronics to receive, store, transmit and manipulate data, said controller providing a graphical interface to the user for access to the operating software thereof, said controller further including a database.

16. The mouth operated input system as recited in claim 15, wherein the second actuator is transitioned intermediate an on and off position via coverage by a portion of a user's lip.

17. The mouth operated input system as recited in claim 16, wherein the third portion of the housing of the activation module includes a receiving member, said receiving member operably coupled with a portion of the joystick present in said cavity of said mounting member.

18. The mouth operated input system as recited in claim 17, wherein the database receives and stores time oriented input data from said joystick module, said first actuator and said second actuator.

19. The mouth operated input system as recited in claim 18, wherein in the second mode, the first actuator and the joystick module require an input value that is less than that of the input value required in the first mode.

20. The mouth operated input system as recited in claim 19, and further including a third mode, in said third mode said activation module is operably coupled to a first device and a second device wherein engagement with the first actuator provides operational input to the first device and engagement with the second actuator or the joystick module provides operational input to the second device.

* * * * *